(12) United States Patent
Ketelhohn

(10) Patent No.: US 6,711,427 B1
(45) Date of Patent: Mar. 23, 2004

(54) SKIN ABRADING MEDICAL ELECTRODE MOUNTING AND PACKAGING SYSTEM

(75) Inventor: Charles H. Ketelhohn, Cedarburg, WI (US)

(73) Assignee: Milwaukee Electronics Corporation, Milwaukee, WI (US)

( * ) Notice: Subject to any disclaimer, the term of this patent is extended or adjusted under 35 U.S.C. 154(b) by 42 days.

(21) Appl. No.: 10/075,660

(22) Filed: Feb. 13, 2002

(51) Int. Cl.$^7$ ................................................ A61B 5/04
(52) U.S. Cl. ..................... 600/372; 600/386; 600/391; 600/392; 607/149; 607/152; 607/153
(58) Field of Search ................................ 600/372, 386, 600/391–394; 607/149, 152, 153

(56) References Cited

U.S. PATENT DOCUMENTS

| | | |
|---|---|---|
| 2,887,112 A | 5/1959 | Smith |
| 3,151,619 A | 10/1964 | Sullivan |
| 3,490,439 A | 1/1970 | Rolston |
| 3,566,860 A | 3/1971 | Moe, Jr. |
| 3,580,240 A * | 5/1971 | Cosentino .................... 600/392 |
| 3,602,216 A | 8/1971 | Moe, Jr. |
| 3,774,592 A | 11/1973 | Lahr |
| 3,805,769 A | 4/1974 | Sessions |
| 3,828,766 A | 8/1974 | Krasnow |
| 3,911,906 A * | 10/1975 | Reinhold, Jr. ................ 600/392 |
| 4,004,578 A | 1/1977 | Palmius |
| 4,027,664 A * | 6/1977 | Heavner et al. ............. 600/376 |
| 4,029,086 A | 6/1977 | Corasanti |
| 4,072,145 A | 2/1978 | Silva |
| 4,126,126 A | 11/1978 | Bare et al. |
| 4,274,419 A | 6/1981 | Tam et al. |
| 4,311,152 A | 1/1982 | Modes et al. |
| 4,459,987 A | 7/1984 | Pangburn |
| 4,595,013 A | 6/1986 | Jones et al. |
| 4,638,807 A | 1/1987 | Ryder |
| 4,640,289 A | 2/1987 | Craighead |
| 4,640,290 A | 2/1987 | Sherwin |
| 4,683,892 A | 8/1987 | Johansson et al. |
| 4,706,679 A | 11/1987 | Schmidt et al. |
| 4,709,702 A | 12/1987 | Sherwin |
| 4,770,180 A | 9/1988 | Schmidt et al. |
| 4,899,754 A | 2/1990 | Bly et al. |
| 4,928,696 A | 5/1990 | Henderson et al. |
| 4,936,306 A | 6/1990 | Doty |
| 4,938,219 A | 7/1990 | Ishii et al. |
| 4,945,911 A | 8/1990 | Cohen et al. |
| 4,967,038 A | 10/1990 | Gevins et al. |
| 4,995,392 A | 2/1991 | Sherwin et al. |
| 5,197,471 A | 3/1993 | Otero |
| 5,211,174 A | 5/1993 | Imran |
| 5,305,746 A | 4/1994 | Fendrock |
| 5,984,102 A | 11/1999 | Tay |
| 6,136,008 A | 10/2000 | Becker et al. |

FOREIGN PATENT DOCUMENTS

JP 6-14894 1/1994

* cited by examiner

Primary Examiner—Lee Cohen
(74) Attorney, Agent, or Firm—Boyle, Fredrickson, Newholm, Stein & Gratz, S.C.

(57) ABSTRACT

A unitary electrode mounting and packaging system for roughening the skin of a patient and applying an electrocardiogram (ECG) monitoring electrode to the skin in a single step. A sheet of a thin plastic material is folded over itself to form a U-shaped carrier having an upper panel connected to a lower panel by the fold. The upper panel supports an electrode and an amount of an electrically conductive gel in a pocket that is covered by the electrode. The lower panel includes an abrasive or roughened material on the bottom surface of the lower panel opposite the electrode. To place the electrode on the skin, the carrier is positioned against the skin of a patient such that the roughened material contacts the skin and pressure is applied downwardly on the electrode. A tab connected to the lower panel then is grasped and pulled by an individual such that the roughened material abrades the skin beneath the carrier to clear the portion of the skin located beneath the electrode. Continued pulling of the tab then deposits the electrically conductive gel and the electrode on the portion of the skin cleared by the roughened material on the lower panel.

18 Claims, 3 Drawing Sheets

SKIN ABRADING MEDICAL ELECTRODE MOUNTING AND PACKAGING SYSTEM

FIELD OF THE INVENTION

The present invention relates to electrocardiogram monitoring electrodes, and more specifically to an improved integral mounting and packaging system for the electrodes.

BACKGROUND OF THE INVENTION

In order to monitor the condition of a patient, electrocardiogram or ECG monitoring electrodes are positioned on the body of a patient in the vicinity of the heart. The electrodes pick up electric signals generated by the heart and transmit the signals to a monitor which provides a visual representation of the heart signals to a physician for analysis of the condition of the heart. The electrodes are designed for a single use and are individually packaged in disposable packages that allow quick access to the electrode contained therein.

In order to provide an accurate representation of the signal for analysis by the physician, the electrodes must be placed in direct electrical contact with the skin of the patient. For the electrodes to be placed in direct electrical contact with the skin, it is desirable to remove the hair and a portion of the epidermis or external skin layer prior to the application of the electrode to the skin of the patient. This is normally accomplished by first cleaning the site to which the electrode is to be applied using rubbing alcohol on a cotton ball. This will remove oils secreted from the skin from the site. After the site is cleaned, a razor is used to remove the hair on the site. Finally, an abrasive pad or equivalent is rubbed against the skin of the individual on the location where the electrode is to be positioned to remove a portion of the epidermis, or the outer layer of the skin. After the hair and epidermis portion have been removed by razor and rubbing the pad against the skin, the electrode may then be positioned on the skin in the prepared location.

To further enhance the electrical contact of the electrode with the skin, an amount of an electrically-conductive gel is utilized with the electrode. The gel can either be applied to the contact side of the electrode or incorporated within the electrode. When the electrode and gel are positioned on the skin, the gel spreads outwardly between the electrode and the skin to provide a conduit between the skin and the electrode to enhance the transmission of electrical signals emitting from the heart of the patient to the electrode.

While the use of the separate abrasive pad and ECG electrode is adequate to provide sufficient electrical contact between the electrode and the skin of the patient, in certain situations the speed of the preparation of the skin using the separate abrasive pad is not fast enough to adequately serve the needs of the patient. For example, in situations where the patient is in cardiac arrest, the application of the ECG electrodes to the skin of the patient in a proper manner needs to be accomplished as fast as possible. As a result, the time needed to properly prepare the skin of the individual using the abrasive pad increases the time needed to properly apply the electrodes to the patient, possibly to the detriment of the patient.

Therefore, it is desirable to develop a simple mounting and packaging system for an ECG electrode which allows a physician or other medical personnel to quickly prepare the skin of the patient and apply the electrode. The improved system should entail a minimal number of steps in preparing the skin, unpackaging the electrode and applying the electrode, so that the minimal amount of time is needed for the application of the electrode to the patient.

Furthermore, since it has recently been found that it is only necessary to abrade or prepare the skin on an electrode application site in order to obtain good electrical contact between the electrode and the skin, it is desirable to develop a self-prepping electrode that can easily prepare the skin of a patient through the hair of the patient.

SUMMARY OF THE INVENTION

It is an object of the present invention to provide an improved mounting and packaging system for an ECG electrode which enables the skin of the patient to be prepared through the hair of a patient and the electrode to be applied to the skin in a single step.

It is another object of the present invention to provide an improved mounting and packaging system for an ECG electrode that can be formed in conjunction with other separable mounting and packaging systems for separate ECG electrodes such that a number of electrodes can be packaged together in a single unit.

It is still another object of the invention to provide an improved mounting and packaging system for an ECG electrode that also contains an amount of an electrically conductive gel that is applied to the skin with the electrode.

It is still a further object of the invention to provide an improved mounting system for an ECG electrode that can be readily modified to accommodate ECG electrodes of various configurations and sizes.

The present invention is an improved mounting and packaging system for an ECG electrode that allows medical personnel to prepare the skin of the patient and apply the electrode in a single step. The system includes at least one carrier formed of a single sheet of a flexible material that includes an upper panel and a lower panel joined to one another by a fold. The upper panel includes a depression over which the electrode is releasably attached. An amount of an electrically conductive gel is disposed within the depression and covered by the electrode. Opposite the electrode, the lower panel includes an abrasive surface that is used to contact and prepare the skin of the patient for the application of the electrode. Opposite the fold, the lower panel of the system further includes a tab that is grasped by an individual in order to utilize the mounting and packaging system and prepare the skin and apply the electrode to the individual in a single step.

To apply the electrode to the patient, the individual places the mounting and packaging system against the skin of the patient such that the abrasive surface of the lower panel of the system contacts the skin of the patient. The individual grasps the electrode to hold the electrode in the desired position over the skin. The individual then grabs the tab on the lower panel and pulls the tab such that the abrasive surface on the lower panel is dragged along the patient's skin, removing a portion of the epidermis from the skin of the patient. Continued pulling of the tab removes the upper panel and exposes the conductive gel disposed within the depression and the electrode such that the gel and electrode are subsequently positioned in contact with the prepared surface of the skin of the individual.

Various alternatives and other embodiments of the invention will become apparent from the following detailed description taken together with the drawings.

BRIEF DESCRIPTION OF THE DRAWINGS

The drawings illustrate the best mode presently contemplated of carrying out the invention.

In the drawings.

DETAILED DESCRIPTION OF THE INVENTION

Figure 1:
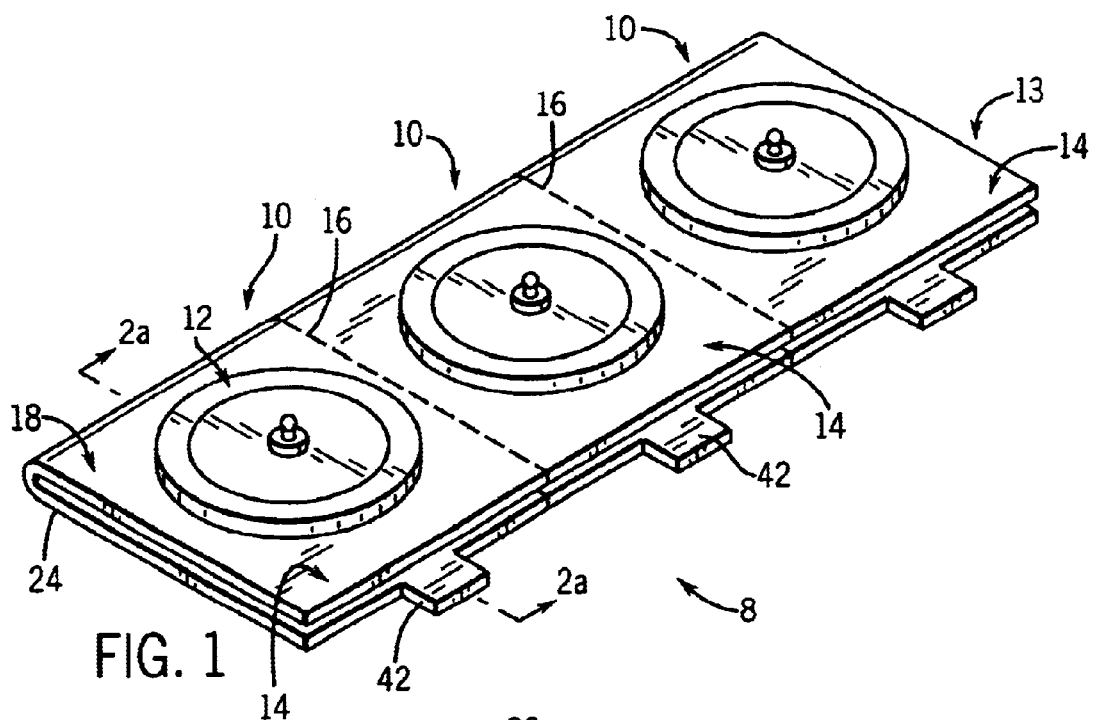
FIG. 1 is an isometric view of a number of carriers forming a mounting and packaging system constructed according to the present invention and supporting a number of ECG electrodes and joined to one another.

With respect now to the following detailed description in which like reference numerals designate like parts throughout the disclosure, an improved ECG electrode mounting and packaging system 8 formed of a plurality of carriers 10 supporting a number of disposable electrodes 12 is illustrated in FIG. 1. The carriers 10 are formed of a piece 13 of flexible material, such as a soft plastic, that is separated into a number of individual sheets 14 by lines of perforation 16 extending between each sheet 14. Other satisfactory materials for the material of carriers 10 include laminated paper.

Figure 2:
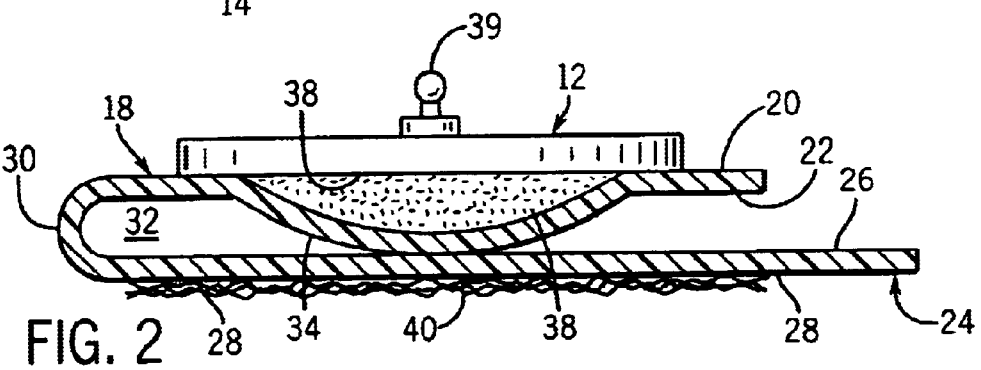
FIG. 2 is a cross-sectional view along line 2—2 of FIG. 1.
Figure 6:
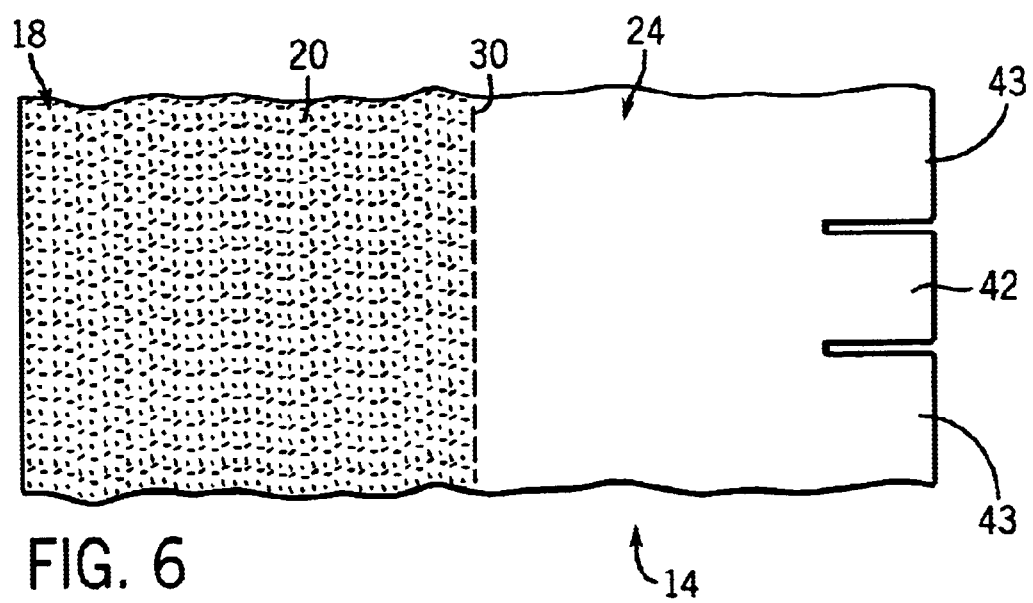
FIG. 6 is a bottom plan view of a sheet forming a carrier of the system of FIG. 1.

Referring now to FIGS. 2 and 6, each sheet 14 includes an upper panel 18 that defines a top surface 20 and a bottom surface 22, and a lower panel 24 which defines a top surface 26 and a bottom surface 28. The upper panel 18 and lower panel 24 are joined by a generally U-shaped fold 30 that extends between adjacent edges of the upper panel 18 and lower panel 24 in order to define a space 32 between the upper panel 18 and lower panel 24.

The upper panel 18 includes a circular, concave pocket or depression 34 disposed in the center of the upper panel 18. The depression 34 extends downwardly from the top surface 20 of the upper panel 18 such that, at the lowermost portion of the depression 34, the bottom surface 22 contacts the top surface 26 of lower panel 24. The depression 34 is filled with an electrically conductive gel 36 which is used to enhance the electrical contact of the electrode 12 with signals transmitted through the skin 37 of the patient. The gel 36 used can be any commercially available electrolyte gel, with a preferred gel being a silver/silver chloride (Ag/AgCl) gel.

The gel 36 is retained within the depression 34 by the placement of the electrode 12 over the top of the depression 34. The electrode 12 is generally circular in shape and has a diameter greater than the diameter of the depression 34 so that the electrode 12 completely covers the depression 34. The electrode 12 is secured to the top surface 20 of the upper panel 18 around the depression 34 by an adhesive (not shown) which is capable of retaining the electrode 12 on the upper panel 18 until the sheet 14 is pulled away from the electrode 12. The electrode 12 includes a contact surface 38 that is disposed in contact with the gel 36 and receives the signals transmitted through the skin 37 of the patient and a contact 39 disposed opposite the contact surface 38. The contact 39 is connected to the contact surface 38 and can be connected to a signal lead wire (not shown) extending from a monitor (not shown) in order to transmit the signal received by the contact surface 38 to the monitor for viewing by medical personnel. The monitor that the electrode 12 is connected to can be any device used to monitor or diagnose an ECG, such as a defibrillator or electrocardiograph, for example. The electrode 12 can be any commercially available ECG monitoring electrode which is made to be disposed of after a single use, such as the electrode Part No. 9431-303 manufactured and sold by Marquette Electronics, Inc. of Jupiter, Fla.

Figure 7:
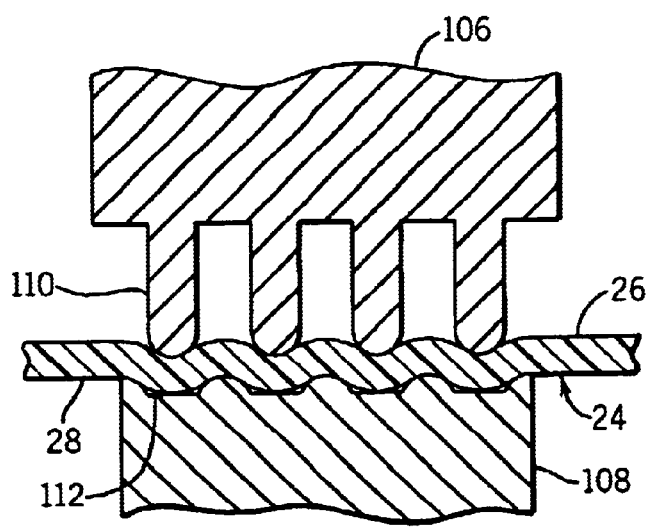
FIG. 7 is a schematic view of the formation of the abrasive surface on the sheet of FIG. 6.

Opposite the upper panel 18, the lower panel 24 includes a roughened, abrasive material or area 40 disposed on the bottom surface 28 of the lower panel 24. The roughened area 40 is used to remove the portion of the epidermis from the skin 37 of the patient. As best shown in FIG. 7, the roughened area 40 can be formed on the bottom surface 28 of the lower panel 24 prior to folding into the configuration for the strip 10 by drawing sheet 14 between an extrusion punch 106 and an extrusion die 108. The punch 106 and die 108 include a number of pins 110 and channels 112, respectively, that engage and deform the bottom surface 28 of the sheet 14 to create the roughened area 40 on the bottom surface 28. Alternatively, the abrasive area may be formed by an abrasive material separate from and applied to bottom surface 28 of the lower panel 24 in a conventional manner. When the abrasive area 40 is formed by an abrasive material separate from the sheet 14, the material can include granules of a hardened substance such as silica or other suitable materials which provide an abrasive property to the bottom surface 28.

The lower panel 24 further includes a tab 42 disposed opposite the fold 30. The tab 42 extends outwardly from the lower panel 24 beyond the side of upper panel 18 opposite the fold 30. The tab 42 is adapted to be grasped by an individual using the carrier 10, as will be explained, to draw the abrasive material 40 across the skin 37 of the patient and apply the gel 36 and electrode 12. The tab 42 is formed on the lower panel 24 by cutting away a pair of end portions 43 from opposite sides at one end of the sheet 14 to form a tab 42 of a desired shape for grasping by an individual to employ the carrier 10.

Figure 3:
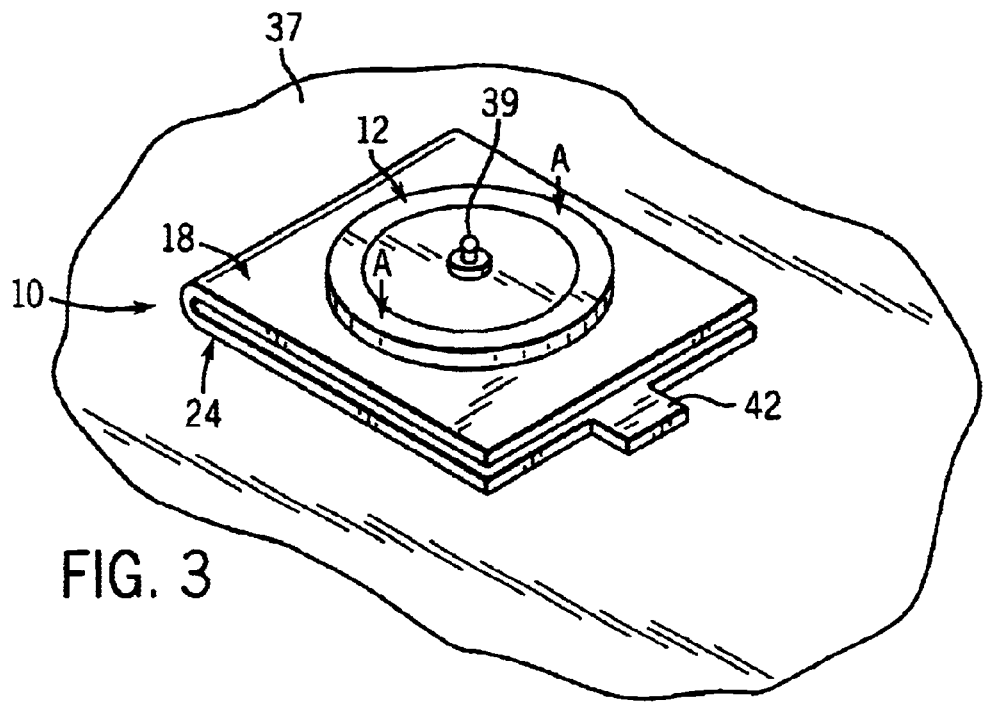
FIG. 3 is an isometric view of the carrier of FIG. 1 applied to the skin of a patient.
Figure 4:
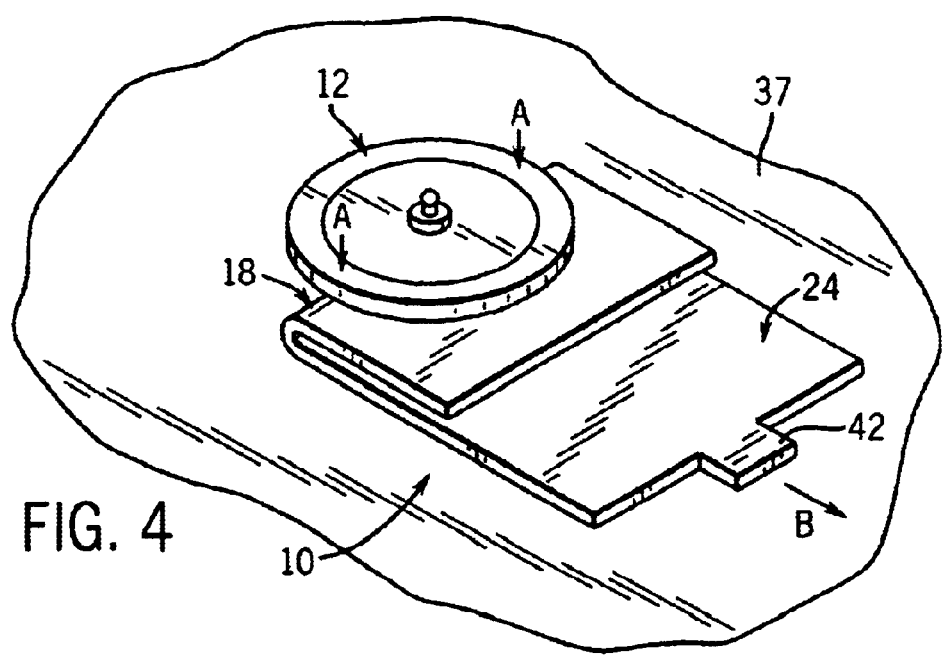
FIG. 4 is an isometric view of the carrier of FIG. 3 illustrating the electrode in a partially mounted position.
Figure 5:
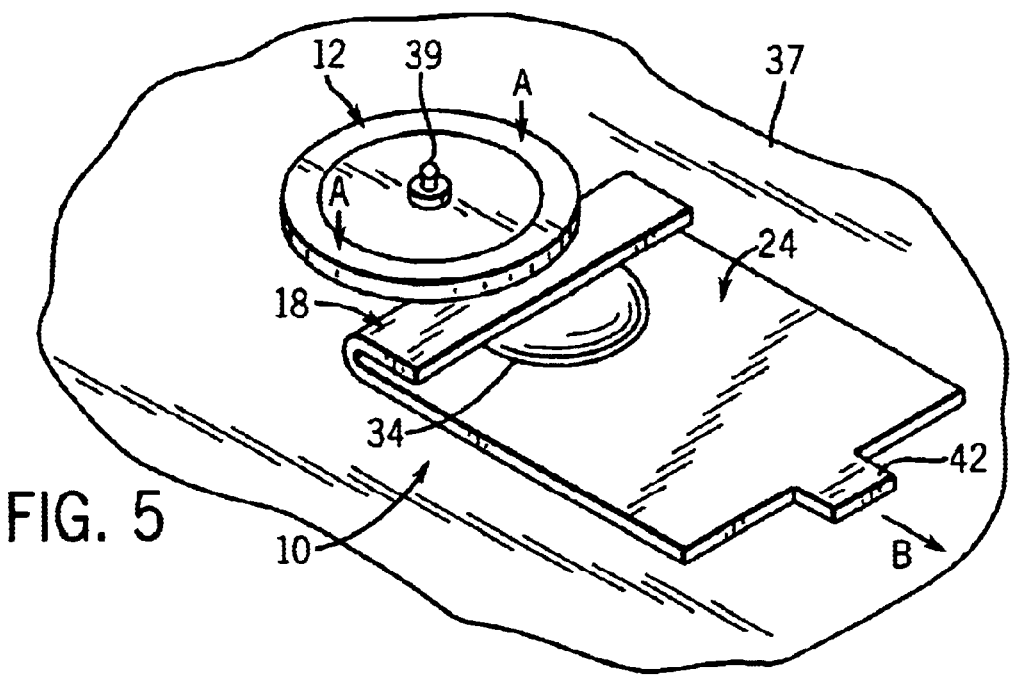
FIG. 5 is an isometric view of the carrier of FIG. 3 with the electrode in a generally fully mounted position.

Referring now to FIGS. 3–5, the operation of the carrier 10 to place the electrode 12 on the skin of the patient is illustrated. Initially, a carrier 10 is detached from the system 8 along the perforation 16. The detached carrier 10 is then positioned on the skin 37 of the patient such that the abrasive area 40 on the lower panel 24 is positioned against the skin 37, with the upper panel 18 and electrode 12 spaced above the skin 37. The individual placing the electrode 12 on the skin 37 then holds the electrode 12 in position by pressing down on opposite sides of the electrode 12, as indicated by the arrows A in FIGS. 3–5. The individual then grasps and pulls the tab 42 on lower panel 24 laterally outwardly in a direction away from the upper panel 18, shown by arrow B in FIGS. 4 and 5, such that the fold 30 is drawn beneath the upper panel 18. In doing so, the roughened area 40 on the bottom surface 28 of the lower panel 24 is drawn across the skin 37 of the patient. As the roughened area 40 moves across the skin 37, it removes an amount of the skin 37 to improve the contact and electrical conductivity between the skin 37 and the contact surface 38 of the electrode 12.

Referring now to FIG. 4, as the tab 42 is pulled to move the lower panel 24 out from beneath the upper panel 18, the depression 34 becomes bent backwards or retracted under the electrode 12, thereby exposing and depositing the gel 36 on the skin 37 of the patient. Simultaneously, upper panel 18 peels away from electrode 12 as fold 30 is drawn below electrode 12, to separate electrode 12 from upper panel 18. Because the individual is holding the electrode 12 in position, the electrode 12 remains directly over the gel 36 when the upper panel 18 is withdrawn and applies the gel 36 between the electrode 12 and the skin 37. Continued pulling on the tab 42 deflects continually more of the depression 34 such that substantially the entire amount of gel 36 is deposited from within the depression 34 onto the skin 37 of the patient between the electrode 12 and the skin 37. The individual continues to pull on the tab 42 until the entire sheet 14 is completely retracted from between the electrode 12 and the skin 37, leaving the electrode 12 and gel 36 disposed on the prepared location on the skin 37. The electrode 12 can then be hooked up to the monitor to display the signals generated by the heart of the patient, while the sheet 14 can be disposed of in a conventional manner.

It can thus be appreciated that carrier 10 provides a simple, efficient and effective arrangement for both packaging electrode 12 and rapidly applying electrode 12 to the skin of a patient. The presence of skin abrading material on lower panel 24 eliminates the need for separate skin abrading supplies, and provides skin abrasion and electrode application in a single step operation.

While the above description illustrates the best mode currently used to practice the invention, other modifications and embodiment are also considered to be part of the invention. For example, the depression 34 can have any size or shape in order to accommodate the desired amount of gel 36. The sheet 14 can also be used to support and position any medical device other than an electrode 12 which requires the skin 37 of the patient to be prepared prior to applying the device.

In addition, it should be understood that the present invention contemplates simultaneous skin abrasion and electrode application in other arrangements than the specifically described components and operation. For example, abrasive area 40 on lower surface 28 of lower panel 24 may be applied to less than the entire area of bottom surface 28, so long as the width of abrasive area 40 corresponds to the diameter of electrode 12. Further, lower panel 24 may have a length greater than that of upper panel 18 so as to increase the length of abrasive area 40, if a greater amount of abrasive is required to attain proper skin abrasion. Further, in an alternative embodiment, it is contemplated that carrier 10 may be in the form of a single panel having electrode 12 mounted to its top surface and having abrasive 40 on its bottom surface. In this type of arrangement, the electrode 12 must release from the panel as the panel is moved laterally from between the electrode and the skin. A system of this type contemplates adhesive release upon application of lateral force, or a separate adhesive carrier which provides adhesive release when a lateral force is applied. This type of arrangement would be especially advantageous upon development of a material which can function both to temporarily adhere the electrode to the packaging material and to also remain with the electrode and perform an electrically conductive function, such that the packaging of conductive gel 36 along with the electrode can be eliminated.

Various alternatives are contemplated as being within the scope of the following claims particularly pointing out and distinctly claiming the subject matter regarded as the invention.

I claim:

1. A medical electrode system, comprising:
    a medical electrode having a contact surface adapted to contact the skin of a patient; and
    an electrode carrier, comprising a top panel interconnected with a bottom panel, wherein the contact surface of the electrode is releasably secured to an upper surface defined by the top panel and wherein the bottom panel defines a downwardly facing surface, and wherein at least a portion of the downwardly facing surface includes an abrasive area.

2. The medical electrode system of claim 1, wherein the top panel and the bottom panel are interconnected by a fold therebetween.

3. The medical electrode system of claim 2, wherein the top panel includes a side edge located on an opposite side of the electrode from the fold between the top and bottom panels, and wherein at least a portion of the bottom panel extends outwardly of the side edge defined by the top panel.

4. The medical electrode system of claim 3, wherein the bottom panel defines a side edge and an outwardly extending tab, wherein the outwardly extending tab comprises the portion of the bottom panel which extends outwardly of the side edge defined by the top panel.

5. The medical electrode system of claim 4, wherein the tab occupies less than the entire length of the side edge defined by the bottom panel.

6. The medical electrode system of claim 2, further comprising a pocket defined by the top panel, wherein at least a portion of the contact surface of the electrode is located over the pocket, and a quantity of conductive fluid contained within the pocket.

7. The medical electrode system of claim 2, wherein the abrasive area of the downwardly facing surface comprises a layer of abrasive material applied to the downwardly facing surface.

8. In a medical electrode package wherein an electrode is releasably secured to a first surface defined by a substantially flat carrier panel, the improvement comprising an abrasive area disposed on a second surface defined by the carrier panel, wherein the second surface faces in a direction opposite that of the first surface, wherein the carrier panel comprises a top wall and a bottom wall with a fold area therebetween, wherein the first surface is defined by the top wall and the second surface is defined by the bottom wall.

9. The improvement of claim 8, wherein the top wall defines a side edge opposite the fold area and a depression between the side edge and the fold area.

10. The improvement of claim 9 wherein the depression holds an amount of a conductive fluid.

11. The improvement of claim 8 wherein the abrasive area is formed integrally with the second surface.

12. The improvement of claim 8 wherein the abrasive area is applied to the second surface.

13. The improvement of claim 8 further comprising a tab extending outwardly from the second surface.

14. A method of applying an electrode to the skin of a patient, the method comprising the steps of:
 a) providing a carrier including an upper panel and a lower panel disposed beneath and interconnected with the upper panel, the upper panel releasably supporting an electrode and the lower panel including an abrasive material opposite the upper panel;
 b) placing the abrasive material on the lower panel against the skin of an individual;
 c) holding the electrode stationary; and
 d) pulling the lower panel and upper panel outwardly from beneath the electrode.

15. The method of claim 14 wherein the step of pulling the lower panel and upper panel from beneath the electrode comprises the steps of:
 a) grasping a tab formed on the lower panel that extends outwardly from beneath the upper panel; and
 b) pulling the tab outwardly in a direction parallel to the upper panel.

16. The method of claim 15 wherein the upper panel includes a pocket located above the lower panel over which the electrode is positioned.

17. The method of claim 16 wherein the pocket contains an electrically conductive fluid.

18. The method of claim 17 further comprising the step of depositing the fluid from within the pocket on the skin of the patient simultaneously with the step of pulling the tab.

\* \* \* \* \*